United States Patent [19]

Nyman

[11] Patent Number: 5,423,879
[45] Date of Patent: Jun. 13, 1995

[54] CONTROLLABLE ELECTRODE DEVICE FOR IN VIVO TISSUE STIMULATION

[75] Inventor: Per Nyman, Djursholm, Sweden

[73] Assignee: Siemens Elema AB, Solna, Sweden

[21] Appl. No.: 108,515

[22] Filed: Aug. 18, 1993

[30] Foreign Application Priority Data

Aug. 28, 1992 [SE] Sweden .................... 9202481

[51] Int. Cl.⁶ .................................. A61N 1/05
[52] U.S. Cl. ................................. 607/122
[58] Field of Search ............ 607/122, 123, 124, 125, 607/128, 131

[56] References Cited

U.S. PATENT DOCUMENTS 4,498,482  2/1985  Williams .
4,677,990  7/1987  Neubauer .
4,791,939  12/1988 Maillard .

FOREIGN PATENT DOCUMENTS 3043189  6/1982  Germany .

Primary Examiner—William E. Kamm
Assistant Examiner—Scott M. Getzow
Attorney, Agent, or Firm—Hill, Steadman & Simpson

[57] ABSTRACT

An electrode device for intracorporeal stimulation of body tissue, particularly for intracardial stimulation of the heart, has an electrode cable containing an elongated, flexible conductor having an exterior covered with a layer of insulation, and an interior forming a channel for the introduction of an elongated member for transmitting a pushing force to the distal (i.e., treatment site) end of the electrode for controlling the configuration of the electrode device as it is inserted in a patient. An electrode head is disposed at the distal end of the conductor. For making the electrode device pliant and elastic to facilitate implantation, even using an inserted stylet which need not be retracted, the elongated member in the interior of the conductor is made longitudinally stiff but has relatively large lateral flexibility.

7 Claims, 1 Drawing Sheet

CONTROLLABLE ELECTRODE DEVICE FOR IN VIVO TISSUE STIMULATION

BACKGROUND OF THE INVENTION

1. Field of the Invention

The present invention relates to a controllable electrode device for intracorporeal stimulation of body tissue, particularly of the type suited for intracardial stimulation of a heart.

2. Description of the Prior Art

Electrode devices are generally known in the art for intracardial stimulation of heart which include an electrode cable containing an elongate, flexible conductor having an exterior provided with a layer of insulation and an interior forming a channel which is capable of receiving an elongated member, such as stylet, for transmitting a pushing force to the distal end of the electrode, at which the electrode head is disposed. As used herein, "distal" means distal relative to a yet-to-be-connected stimulation device, or alternatively, that end of the electrode disposed at the treatment site.

In electrode devices of this type, it is of great importance for the electrode cable to be sufficiently pliant so that it is able, during advancement during implantation into a patient's heart via a vein, to follow the course of the vein without damaging the venous wall. In most instances, the electrode cable is introduced using a stylet, which is inserted into a channel inside the cable, and which is made of a material which achieves the desired stiffness necessary to advance the electrode cable in a vein. At difficult passages, for example, where the cable must bend sharply, the stylet is often retracted slightly, so that the distal end of the electrode cable displays maximum pliancy. After such a passage has been negotiated, the stylet is again advanced to the distal end of the electrode cable in order to push this end, for example, into the atrium or ventricle until the electrode head bears against the heart wall, for stimulation of the heart. When the electrode is in place, the stylet is withdrawn, which is a procedure that may damage the conductor, which often forms the channel for the stylet, at the locations of sharp bends in the vein in which the electrode cable has been inserted.

An electrode device of this type, having an electrode cable which is advanced in a vein with the aid of a stylet, is described, for example, in German OS 3 043 189.

Another electrode device of this type is described in the U.S. Pat. No 4,677,990. The stylet described therein is thinner at its anterior end than along the rest of the stylet, so the distal end of the cable can be bent into a J-shape.

SUMMARY OF THE INVENTION

It is an object of the present invention to provide an electrode device having an electrode cable with a conductor having a channel therein for receiving an insertion instrument, such as a stylet, which is relatively pliant and elastic, even with the stylet in place.

It is a further object of the present invention to provide such an electrode device wherein the stylet does not need to be retracted during advancement of the electrode cable through a vein.

The above objects are achieved in accordance with the principles of the present invention in an electrode device wherein the elongated, insertion member is longitudinally stiff while having relatively great lateral flexibility. As used herein, "longitudinal" means the direction along which the electrode device is to be inserted in a vein, and "lateral" means directions substantially perpendicular to the longitudinal direction. When the elongated member (stylet) is inserted into the channel of the electrode cable, the stylet is laterally supported by the conductor and the layer of insulation. Because the stylet is longitudinally stiff, it can impart the pushing force to the distal end of the electrode cable required for electrode advancement. With the use of a stylet having relatively great lateral flexibility and pliancy, the stylet does not have to be retracted within the electrode cable during the passage of difficult locations in the vein.

In a simple embodiment of the invention, the elongated member is a wire consisting of plastic material. The wire may be made, for example, of nylon.

In a preferred embodiment of the invention, the elongated member consists of at least two intertwined wires. This results in very great lateral flexibility with relatively great longitudinal stiffness.

The intertwined wires may be made of metal or of a plastic material.

In a further embodiment of the invention, the elongated member consists of a relatively thin wire, on which relatively stiff tubular or ring-shaped elements are strung over most of the length of the wire. One end of the wire is provided with a stop for the tubular or ring-shaped elements. This results in a stylet which can be changed from being extremely stiff to one being extremely pliant. This stylet does not require any lateral support. The tubular or ring-shaped elements can consist of a stiff material, or a combination of several still materials. For example, the distal end of the stylet may be provided with elements which are somewhat softer than the other elements, so that the distal end is more flexible in the passage through a vein.

In another embodiment of the invention, the stop may be an elongated element consisting of a relatively soft material. In this manner, the distal end of the electrode cable can be made very pliant.

DESCRIPTION OF THE PREFERRED EMBODIMENTS

Figure 1:
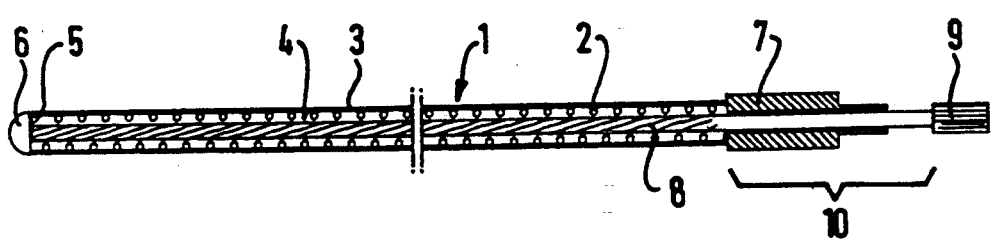
FIG. 1 is a side view, in cross-section, of an electrode device embodying a stylet constructed in accordance with the principles of the present invention.

An electrode device for intracardial stimulation of a heart is shown in FIG. 1. The electrode device included an electrode cable 1 containing an elongated, flexible conductor 2 having an exterior provided with a layer of insulation 3 and an interior forming a channel 4. An electrode head 6 is disposed at a distal end 5 of the conductor 2 for stimulating heart tissue in a patient. The electrode cable 1 also contains a connector part 7 for electrically and mechanically connecting the cable 1 to a heart stimulation apparatus (not shown).

A stylet 8, consisting in this embodiment of at least two intertwined wires, is inserted in the channel 4. The wires may consist of metal or a plastic material. The proximal end of the stylet 8 is equipped with a handle 9.

A portion 10 of the stylet 8 next to the handle 9 is laterally stiffened in this embodiment with, for example, solder (if the stylet 8 is made of metal) or with glue (if the stylet 8 is made of a plastic material). Such stiffening can be advantageous, especially if this part of the stylet 8 is outside of the electrode cable 1 and is therefore not laterally stiffened by the conductor 2 and the layer of insulation 3. When the electrode cable 1 must be pliant, particularly at its distal end and midsection, other portions of the stylet 8 can be stiffened in the same manner.

In another embodiment, not shown in the drawings, the stylet may consist of a homogenous plastic material, such as nylon, with properties making it longitudinally stiff but with relatively great lateral flexibility.

Figure 2:
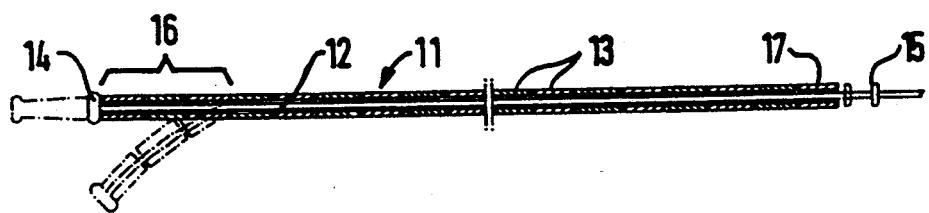
FIG. 2 is a side view, in cross-section of a further embodiment of a stylet constructed in accordance with the principles of the present invention, for use in an electrode device as shown in FIG. 1.

Another stylet 11 is shown in FIG. 2. The stylet 11 consists of a relatively thin wire 12, on which relatively stiff tubular or ring-shaped elements 13 are strung, the elements 13 extending over the length of the wire 12. The distal end of the wire is equipped with a stop 14 for the elements 13. The proximal end of the wire 12 is equipped with an additional stop 15 for the elements 13. The stop 15 can be slidably arranged on the wire 12. In order to achieve a soft distal end, the element or elements 13 at the portion 16 of the stylet 11 closer to the distal end can be made of material which is somewhat softer than the other elements 13. Alternatively, the stop 14 amy be in the form of an elongated element made of a softer material than the elements 13. This version is shown in FIG. 2 in dashed lines.

When the stylet 11 as shown in FIG. 2 is placed inside the channel 4 in the electrode cable 1 (shown in FIG. 1), the stiffness of the electrode cable 1 can be controlled by the operator advancing the stop 15 against the proximate-most element 17, or holding onto the element 17 at the same time as the operator pulls on the wire 12. This presses the elements 13 together, thereby stiffening the stylet 11. When the operator releases pressure so the wire 12 slackens, the stylet 11, and accordingly the electrode cable 1, become more pliant. This is shown in FIG. 2 by the dashed lines indicating the distal portion 16 of the stylet 11.

The invention is not limited to the embodiments shown and described herein. The basic inventive concept is to provide a stylet which is longitudinally stiff because of the electrode lateral support provided by the electrode cable, but which also displays great lateral flexibility. The primary advantage of the invention disclosed herein is to facilitate advancement of the electrode cable in a vein, compared to advancement which can be achieved with prior art electrodes using a stylet.

Because the electrode cable disclosed herein can be advanced in a vein with virtually no loss of pliancy, the risk of undesirable venospasm, injuries to veins, and incorrect introduction into coronary vessels and inferior veins, such as the inferior vena cava, is reduced. With a laterally flexible stylet, the risk of damage to the conductors of the electrode cable when the stylet is withdrawn from the electrode cables channel is also reduced.

Although modifications and changes may be suggested by those skilled in the art, it is the intention of the inventor to embody within the patent warranted hereon all changes and modifications as reasonably and properly come within the scope of his contribution to the art.

We claim our invention:

1. A controllable electrode device for intracorporeal stimulation of body tissue comprising:
    an electrode cable including an elongated, flexible, conductor having an exterior covered by a layer of insulation and an interior forming a channel having a length, said electrode cable having a distal end at which an electrode head is disposed, and a proximate end opposite thereto; and
    an elongated insertion member disposed in said channel for transmitting a pushing force from said proximate end to said distal end of said electrode cable, said elongated member having a longitudinal length substantially co-extensive with said length of said channel and being stiff along substantially its entire longitudinal length and having substantial lateral flexibility in directions substantially perpendicular to said longitudinal length.

2. A controllable electrode device as claimed in claim 1 wherein said elongated member comprises a wire consisting of plastic material.

3. A controllable electrode device as claimed in claim 1 wherein said elongated member consists of at least two intertwined wires.

4. A controllable electrode device as claimed in claim 3 wherein said wires consist of plastic material.

5. A controllable electrode device as claimed in claim 3, wherein said wires consist of metal.

6. A controllable electrode device as claimed in claim 1 wherein said elongated member consists of a thin wire having a plurality of stiff tubular elements strung thereon over substantially all of the longitudinal length of said wire, and a stop disposed at a distal end of said wire for preventing further movement of said tubular elements along said wire.

7. A controllable electrode device as claimed in claim 6, wherein said stop consists of an elongated element consisting of pliant material.

* * * * *